United States Patent
Paehl et al.

(10) Patent No.: US 10,064,704 B2
(45) Date of Patent: Sep. 4, 2018

(54) METHOD OF MAKING CUSTOMIZED ORTHODONTIC BRACKETS

(71) Applicant: 3M INNOVATIVE PROPERTIES COMPANY, St. Paul, MN (US)

(72) Inventors: Ralf M. Paehl, Melle (DE); Ralf Schlimper, Melle (DE)

(73) Assignee: 3M Innovative Properties Company, St. Paul, MN (US)

( * ) Notice: Subject to any disclaimer, the term of this patent is extended or adjusted under 35 U.S.C. 154(b) by 187 days.

(21) Appl. No.: 15/101,831

(22) PCT Filed: Dec. 4, 2014

(86) PCT No.: PCT/US2014/068496
§ 371 (c)(1),
(2) Date: Jun. 3, 2016

(87) PCT Pub. No.: WO2015/085030
PCT Pub. Date: Jun. 11, 2015

(65) Prior Publication Data
US 2016/0302884 A1    Oct. 20, 2016

(30) Foreign Application Priority Data
Dec. 6, 2013 (EP) .................................. 13195980

(51) Int. Cl.
| | |
|---|---|
| *A61C 7/00* | (2006.01) |
| *A61C 7/14* | (2006.01) |
| *B33Y 50/02* | (2015.01) |
| *G05B 15/02* | (2006.01) |

(52) U.S. Cl.
CPC ................ *A61C 7/002* (2013.01); *A61C 7/14* (2013.01); *B33Y 50/02* (2014.12); *G05B 15/02* (2013.01)

(58) Field of Classification Search
CPC .. A61C 7/00; A61C 7/002; A61C 7/12; A61C 7/14; A61C 7/141–7/145; A61C 13/0004; A61C 13/0006
See application file for complete search history.

(56) References Cited

U.S. PATENT DOCUMENTS

| | | |
|---|---|---|
| 8,636,505 B2 | 1/2014 | Fornoff |
| 9,198,739 B2 | 12/2015 | Vu |

(Continued)

FOREIGN PATENT DOCUMENTS

| | | |
|---|---|---|
| DE | 102011003894 | 8/2012 |
| EP | 1728485 | 3/2010 |

OTHER PUBLICATIONS

International Search Report for PCT International Application No. PCT/US2014/068496 dated May 13, 2015, 5 pages.

*Primary Examiner* — Jun Yoo

(57) ABSTRACT

A method of making customized orthodontic brackets. The method has steps of providing a plurality of customized orthodontic bracket precursors, providing one or more support structures, positioning the bracket precursors by means of the support structure(s) in a machining device and using the machining device to provide an archwire slot in each bracket precursor by material removal with the archwire slots aligned along a common path with each other. The invention helps minimizing efforts in the manufacturing and provides the brackets with a precise archwire slot.

17 Claims, 2 Drawing Sheets

(56) References Cited

U.S. PATENT DOCUMENTS

| | | | |
|---|---|---|---|
| 2002/0006597 A1* | 1/2002 | Andreiko | A61C 7/00 |
| | | | 433/24 |
| 2003/0152884 A1 | 8/2003 | Wiechmann | |
| 2007/0178423 A1* | 8/2007 | Rubbert | A61C 7/00 |
| | | | 433/24 |
| 2012/0015315 A1 | 1/2012 | Wiechmann | |
| 2012/0123577 A1* | 5/2012 | Chapoulaud | A61C 7/00 |
| | | | 700/98 |
| 2013/0313131 A1 | 11/2013 | Vu | |

* cited by examiner

METHOD OF MAKING CUSTOMIZED ORTHODONTIC BRACKETS

CROSS REFERENCE TO RELATED APPLICATIONS

This application is a national stage filing under 35 U.S.C. 371 of PCT/US2014/068496, filed Dec. 4, 2014, which claims the benefit of European Application No. 13195980.1, filed Dec. 6, 2013, the disclosure of which is incorporated by reference in its/their entirety herein.

FIELD OF THE INVENTION

The invention relates to a method of making a customized orthodontic bracket, and in particular to a method in which a plurality of customized orthodontic bracket precursors are provided by a build-up process, and which by help of support structures provided in the build-up process are jointly provided with archwire slots by material removal. The invention further relates to a customized orthodontic bracket obtained by the method of the invention.

BACKGROUND ART

Orthodontic brackets are generally used in orthodontic treatments for moving one or more teeth from an initial position to a desired position in a patient's dentition. The initial position typically refers to a position at the beginning of an orthodontic treatment, for example a position in which the labial faces of the teeth are misaligned to each other, whereas in the desired position the labial faces of the same teeth may be generally aligned. For example the patient's teeth may be aligned relative to each other to provide the dentition with a more aesthetically pleasant appearance. Further one or more teeth may be moved within the dentition to compensate for a malocclusion. Such a movement of a tooth or teeth can be typically achieved by using one or more brackets attached to one or more teeth. The brackets are typically connected to an elastic archwire for applying a force to the teeth toward the desired position over a longer term.

Often orthodontic brackets are off-the-shelf products which are designed to for use with clinical situations of different patients. Further there are customized orthodontic brackets which are typically made to fit with an individual clinical situation of one particular patient.

For example US 2012/0015315 A1 discloses a customized orthodontic bracket system which includes a bracket having a customized bracket bonding pad for bonding the bracket to a tooth of a patient and a bracket slot adapted to receive a customized archwire. The customized archwire is adapted to be positioned in the bracket slot to form a precise bracket slot-archwire interface.

Although a variety of different brackets and bracket systems are on the market there is still a desire to provide brackets which on the one hand match an individual clinical situation and on the other hand are minimized in costs for manufacturing and costs for application to a patient's teeth. Typically the minimization of costs in the manufacturing must be balanced relative to the desired accuracy of the customized brackets. For example, brackets should be placeable easily and precisely to a patients teeth, and should have a geometry allowing an orthodontic archwire to be attached precisely at desired positions relative to the teeth. Further customized brackets should be sufficiently durable over the time period of an orthodontic treatment. On the other hand available manufacturing methods for mass production of customized brackets may not be compatible with such precision and quality requirements, whereas available sufficiently precise and high quality manufacturing methods may not satisfy or fully satisfy requirements for mass production at minimized costs.

SUMMARY OF THE INVENTION

In one aspect the invention relates to a method of making customized orthodontic brackets. The method comprising the steps of:
  providing a plurality of individually shaped customized orthodontic bracket precursors;
  providing one or more support structures;
  positioning the bracket precursors by means of the support structure(s) in a machining device;
  using the machining device to provide an archwire slot in each bracket precursor by material removal with the archwire slots aligned along a common path with each other, and thereby provide a plurality of brackets; and
  separating the support structure(s) and the brackets from each other.

The invention provides advantages in the manufacturing of customized orthodontic brackets. In particular the invention helps minimizing efforts in the making of the brackets and also specifically helps maximizing the precision of the archwire slot of the bracket. The invention allows for example building up the brackets using a rapid prototyping technique at minimized costs, sufficient overall precision and using a relatively inexpensive material (for example steel), and nevertheless allows providing the bracket with an archwire slot having a maximized precision. It has been found that the precision of the archwire slot is important for a successful and rapid orthodontic treatment. In particular a customized bracket system using a rectangular archwire, allowing not only a movement by lateral forces but also a rotation of teeth by torque, the brackets should be dimensioned so that there is neither too much play between the archwire and the archwire slots nor should the archwire sit overly tight in the archwire slots. The invention helps providing brackets which meet such requirements and further help achieving minimized costs in manufacturing.

For the purpose of the present specification a "bracket precursor" relates to a semi-finished bracket having no archwire slot or a preliminary archwire slot being undersized relative to the archwire slot at its desired final geometry. Further a "bracket" as referred to in this specification relates to a bracket having an archwire slot at its desired final geometry. Such a bracket has a bracket bonding pad and a bracket body and the archwire slot is provided in the bracket body.

In an embodiment the method comprises the step of providing a support structure for each bracket precursor. The method may further comprise the step of providing a plurality of support structures for each bracket precursor. The bracket precursor and the support structure are preferably monolithically formed. A support structure as referred to in this specification may be in the form of a protrusion extending from the bracket. In one embodiment the protrusion is a pin, for example a pin extending at a generally uniform cross-section (for example circular or rectangular) along a linear axis. Several support structures preferably end on a common virtual plane or surface. Preferably at least three such pins may be used as support structures for one bracket precursor. Thus the support structures allow a defined positioning and orientation of the bracket precursor on a (planar) surface.

In a further embodiment the method comprises the step of providing a predetermined breaking point between the bracket precursor and the support structure. Thus the bracket precursor (or bracket) and the support structure are adapted for separation from each other by breaking the predetermined breaking point. The predetermined breaking point may be formed for example by a constriction in the pin or pins located adjacent the bracket.

In one embodiment the bracket precursors are positioned in the machining device consecutively in a row. The bracket precursors thereby are preferably positioned and oriented by means of the respective support structures such that the position and orientation of the archwire slot intended to be provided in the bracket precursor are aligned relative to each other.

In a further embodiment the archwire slot in each bracket precursor is provided by grinding. Grinding is preferably performed based on a linear relative movement between a grinding tool and the bracket precursors along the row. For example a grinding wheel may be used to cut the slots straight though all bracket precursors.

In a further embodiment the archwire slot in each bracket precursor is provided by electrical discharge machining of multiple or all bracket precursors at a time. For electrical discharge machining a generally linear structure or wire which extends along the row may be used, for example to cut the slots straight though all bracket precursors.

In a further embodiment the method comprises the steps of:
building up the (or one of the) support structure using additive material manufacturing; and
building up the bracket precursor on the support structure using additive material manufacturing.

In case a bracket precursor comprises a plurality of support structures the method may comprise the steps of:
building up the support structures using additive material manufacturing; and
building up one of the bracket precursors on the support structures using additive material manufacturing.

Preferably building up the support structure(s) and building up the bracket precursor(s) are performed using the same using additive material manufacturing, like for example selective laser melting.

In one embodiment the step of building up the bracket precursor(s) comprises building up a bracket bonding pad on the support structure and a bracket body precursor on the bonding pad. The bracket bonding pad preferably comprises a tooth facing surface oriented toward the support structure and an opposite rear surface supporting the bracket body precursor. The bracket body precursor may comprise an undersized (preliminary) slot forming a basis for providing the archwire slot by material removal from the bracket precursor, particularly from the bracket body precursor.

In a further embodiment the method comprising the steps of:
providing at least one virtual tooth surface of a patient;
providing a virtual bracket comprising a virtual bracket bonding pad and a virtual bracket body, the virtual bracket bonding pad having a virtual tooth facing surface being associated to the virtual tooth surface;
determining a geometric relationship between at least two of:
an archwire position (or archwire slot position),
the bracket position and
a reference surface; and
determining a geometry of a support structure based on the determined geometric relationship.

In a further embodiment the method comprising the step of creating the support structure between the reference surface and the virtual bracket bonding pad.

A computer based method of designing a customized orthodontic bracket as may be used also with present invention is for example disclosed in US 2012/0015315 A1. Such a method is based on capturing the shape of a patient's dentition, for example using a scanner. The dentition may for example be scanned intra-orally or from a plaster model obtained via a dental impression taken from the patient's dentition. The captured shape of the patient's dentition may be stored in the form of a three-dimensional computer representation in a computer that is equipped with computer aided design (CAD) software. The CAD software may be used to simulate the orthodontic treatment, for example the CAD software may store the patient's virtual dentition in an initial position (for example in malocclusion) and may further store the patient's virtual dentition in a desired position (after the treatment). The patient's virtual dentition in the desired position may be obtained by computer aid based on the patient's virtual dentition in the initial position or may be scanned from a so-called set-up model (a physical model in which the teeth have been repositioned manually toward the desired position). Based on the patient's virtual dentition in the initial and the desired position an archwire shape may be designed in relation the virtual dentition.

Further the virtual dentition may be used to define bonding areas for brackets on individual teeth. This may be done by an operator by manually marking such area on individual teeth of the virtual dentition. Each marked area on a tooth of the virtual dentition may be used to create a correspondingly shaped virtual tooth facing surface for a bracket intended to be attached to that tooth. A virtual bracket bonding pad may be provided by creating a three-dimensional virtual object based on the virtual tooth facing surface an offset of the virtual tooth facing surface.

Finally a virtual bracket body may be created as a three-dimensional connector object between the archwire and the boding pad. Because the shape and position of the archwire is defined relative to the virtual dentition a position and orientation of a virtual archwire slot for receiving the archwire can be determined in the virtual bracket body.

A so created virtual bracket precursor comprises at least the bracket bonding pad and the bracket body, and may be provided to a build-up machine, for example a selective laser melting device, for building up the bracket precursor. According to the invention one or more support structures may be included in the design of the bracket precursor so that the bracket precursor may be built up including the support structures.

A virtual structure as used in this specification preferably refers to a mathematic model representing such structure. For example the terms "virtual dentition", "virtual tooth surface", "virtual bracket", "virtual bracket bonding pad" and "virtual bracket body" preferably further refer to a computer representation of a physical "dentition", "tooth surface", "bracket", "bracket bonding pad" and "bracket body", respectively.

In an embodiment the step of providing the bracket precursors involves three-dimensionally building up the bracket precursors in a three-dimensional build-up device which is based on Selective Laser Melting (SLM) or Stereo Lithography (STL).

In one embodiment the bracket precursors are built up from a cobalt-chrome steel or gold.

In a further embodiment the method comprises the steps of:
  providing a support plate which forms the reference surface;
  positioning the support plate in the build-up device; and
  building up the support structure and the bracket precursor.

The support plate may be formed as a common support plate for a plurality of bracket precursors and corresponding support structures, or as individual support plates for a single bracket precursor and corresponding support structure(s). The individual support plates may be configured for combination with each other to form one composed common support plate.

In one embodiment the method further comprises the steps of:
  placing the support plate with the bracket precursors built up thereon in the machining device; and
  providing the bracket precursors with the archwire slot.

In a further aspect the invention relates to a customized orthodontic bracket, obtained by the method of the invention. Such a customized orthodontic bracket preferably is obtained from three-dimensionally building-up or casting and has an archwire slot obtained from material removal.

DETAILED DESCRIPTION OF THE INVENTION

Figure 1:
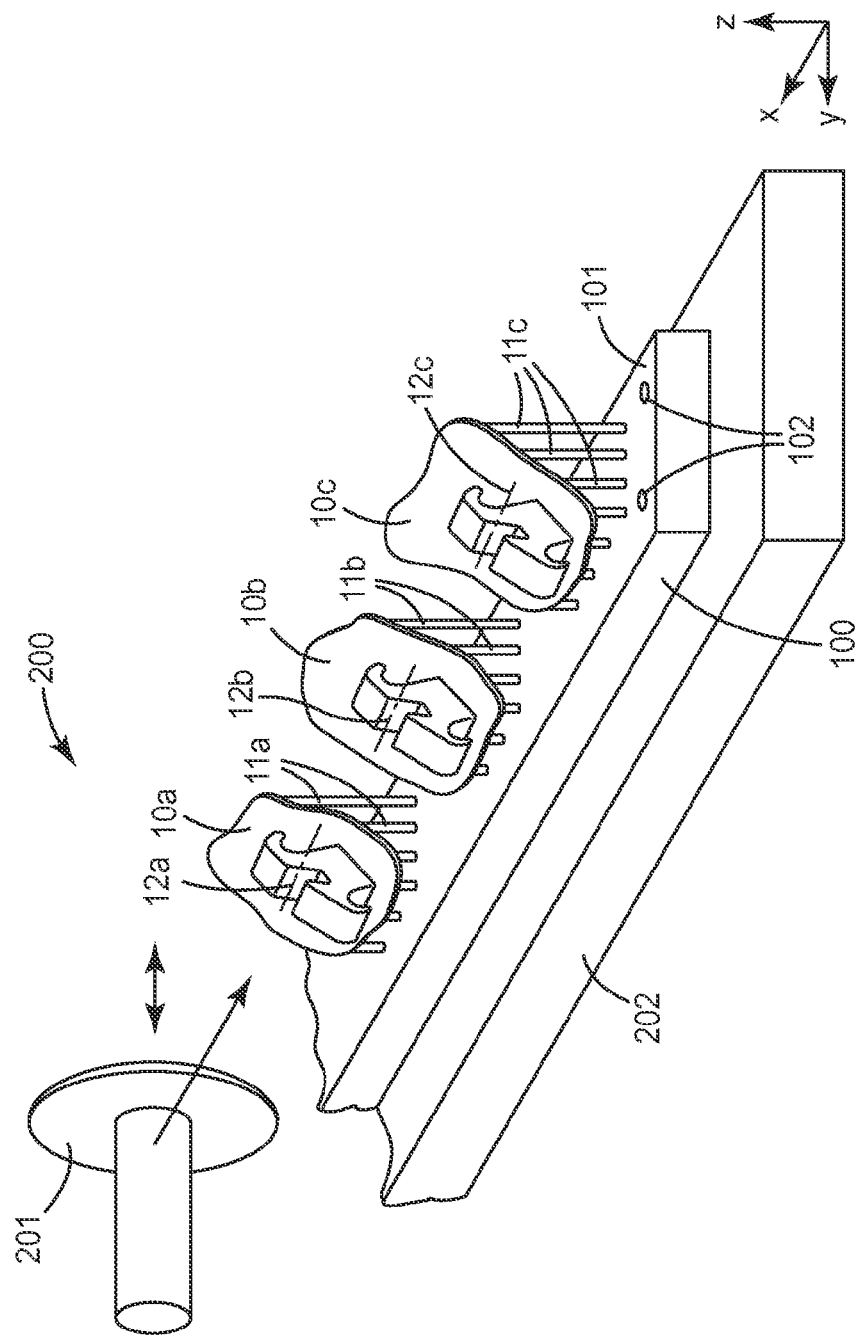
FIG. 1 is a perspective view illustrating a situation in a method according to an embodiment of the invention.

FIG. 1 shows a grinding machine 200. The grinding machine 200 has a rotatable grinding wheel 201 and a machine table 202. The grinding machine 200 is configured such that the grinding wheel 201 and the machine table 202 are linearly movable relative to each other. A similar grinding machine is also known in the field of tool making as "surface grinding machine". However the grinding machine 200 according to the invention is equipped with grinding wheel 201, for example with an ultrathin grinding wheel. The thickness of the grinding wheel 201 is between about 0.1 mm and about 0.4 mm. Such grinding wheel preferably has a polymeric binder to prevent breaking during grinding. A suitable grinding wheel is for example available under the designation type 34 from Finzler, Schrock & Kimmel GmbH, Germany A support plate 100 is positioned in the grinding machine 200. A plurality of bracket precursors 10a, 10b, 10c are arranged on a top surface 101 of the support plate 100. Each of the bracket precursors 10a, 10b, 10c are positioned and supported on the support plate 100 by support structures 11a, 11b, 11c. In the example the support structures 11a, 11b, 11c are in the form of pins extending between the top surface 101 of the support plate 100 and the bracket precursors 10a, 10b, 10c.

The bracket precursors 10a, 10b, 10c, by means of the support structures, are positioned and oriented on the support plate 100 at a predetermined position and orientation relative to the top surface 101 of the support plate 200. The position and orientation is predetermined such that the position and orientation of desired archwire slots in each of the bracket precursors 10a, 10b, 10c are in line with each other. In particular the bracket precursors 10a, 10b, 10c are arranged such that axes 12a, 12b, 12c of the desired archwire slots are coaxial. Thus the archwire slots can be ground in all bracket precursors 10a, 10b, 10c in one and the same grinding cycle. During such grinding cycle the bracket precursors 10a, 10b, 10c and the grinding wheel 201 are moved linearly relative to each other such that the grinding wheel 201 grinds portions from the bracket precursors 10a, 10b, 10c to successively form the archwire slots in all bracket precursors 10a, 10b, 10c. The skilled person will understand that although the overall movement between the bracket precursors 10a, 10b, 10c and the grinding wheel 201 is linear, infeed movements are included in the grinding cycle to provide the archwire slot with desired dimensions.

In another example (not illustrated) the archwire slot is provided by Electrical Discharge Machining In this example a wire, or other appropriate straight structure, is used to machine the archwire slots in multiple bracket precursors at a time.

The support plate 100 preferably has a reference structure for positioning the support plate 100 at a known position and orientation in the grinding machine. Such a reference structure may for example comprise one or more holes 102 in the support plate which are engageable by appropriately fitting alignment pins (not visible) of the grinding device. Further the bracket precursors 10a, 10b, 10c are preferably arranged on the support plate at a predetermined position and orientation relative to the reference structure. Thus—because the position and orientation of the bracket precursors relative to the grinding machine may be known—the grinding wheel 201 of the grinding machine 200 may be easily positioned for grinding the archwire slots at the desired position and orientation in the bracket precursors 10a, 10b, 10c.

In another example (not shown) two or more support plates each carrying one or more bracket precursors may be used instead of a common support plate 100 as shown. Such multiple support plates may be adapted such that they can be combined in a predetermined alignment with each other, for example to form a composed common support plate. Further the support structures may be configured such that a plurality of bracket precursors can be directly aligned with each other. In this case a support plate may not be necessary. In still another example (not shown) the support plate may comprise the support structure(s) for supporting one or more bracket precursors. Such a support plate may carry support structures built up from a relatively inexpensive material, for example a wax or polymer, whereas the bracket precursors may be made of a metal (for example gold or steel) or ceramics.

Figure 2:
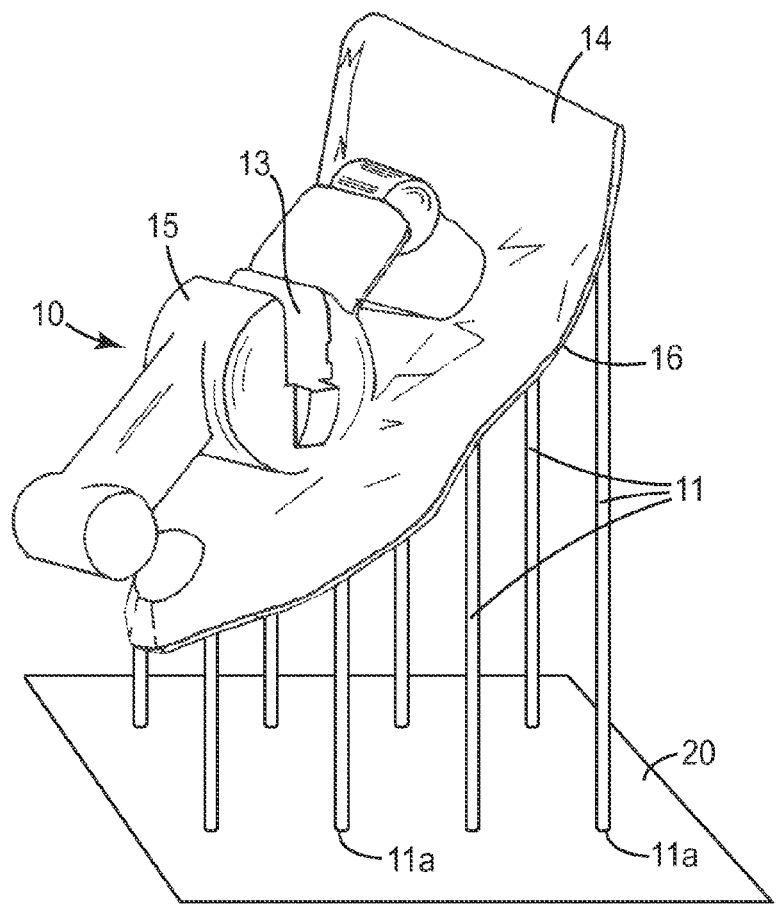
FIG. 2 is a perspective view of a bracket precursor with support structures according to an embodiment of the invention.

FIG. 2 shows a bracket precursor 10 which has a plurality of support structures 11. The bracket precursor 10 in the example has a preliminary slot 13, although such preliminary slot may not be present in other examples. The preliminary slot 13 is undersized with respect to a final archwire slot and may help reducing the time for machining or grinding the archwire slot toward its desired dimensions. Further the bracket precursor 10 has a bonding pad 14 from which the support structures 11 protrude. In particular the support structures 11 protrude from a tooth facing surface 16 of the bracket precursor 10. Each of the support structures 11 has a free end 11a on a common virtual reference surface (in the example a virtual reference plane) 20. Thus the plurality of support structures 11 in combination form an overall planar support allowing the bracket precursor to be positioned on a planar surface (for example on the support plate 100 in FIG. 1). The bracket precursor 10 and the support structures 11 in the example are obtained from building up by a Selective Laser Melting process, for example using a chrome-cobalt steel or gold. Accordingly the bracket precursor 10 and the support structures 11 are monolithically formed in one piece.

Figure 3:
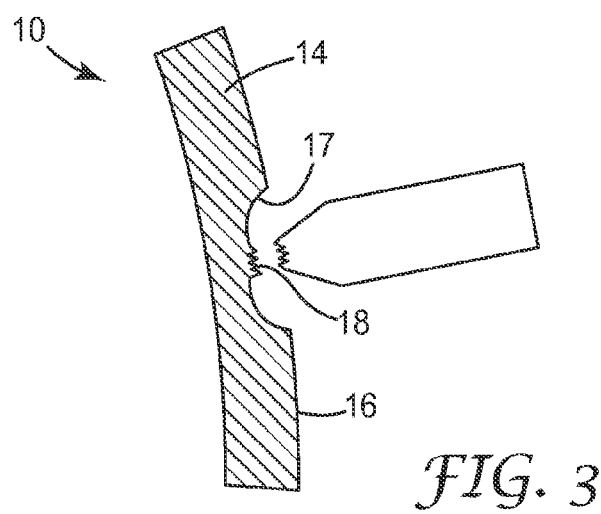
FIG. 3 is a cross-sectional detail view based on the bracket precursor with support structures shown in FIG. 2.

FIG. 3 shows a portion of the bonding pad 14 of the bracket precursor 10 and a support structure 11 separated (broken off) from the bracket precursor 10. The tooth facing surface 16 has cavities 17 (one of which is shown in detail). The support structures 11 originally (before separation) protrude from a surface portion of the cavities 17 and preferably have a predetermined breaking point adjacent that cavity surface portion. In the example the predetermined breaking point is formed by a narrowed portion in the support structure 11. As schematically illustrated, therefore a remaining fracture portion 18 residing after breaking off the support structure 11 preferably does not protrude outside the opening of the cavity 17. Therefore the bracket bonding pad 14 is configured such that any fracture portion 18 of the support structures 11 do not collide or substantially collide with a tooth surface to which the bracket bonding pad may be adhered. And thus any residing fracture portion 18 may not affect mounting the finished bracket to a patient's tooth. The cavities and breaking points may further provide additional surface and structure to improve bond strength after bonding the bracket with the tooth facing surface to a patient's tooth.

The invention claimed is:

1. A method of making customized orthodontic brackets, the method comprising the steps of:
 providing a plurality of individually shaped customized orthodontic bracket precursors;
 providing a support structure for each bracket precursor;
 positioning the bracket precursors with the support structures in a machining device;
 using the machining device to provide an archwire slot in each bracket precursor by material removal, thereby providing a plurality of archwire slots with the archwire slots aligned along a common path with each other, and thereby providing a plurality of brackets; and
 separating the support structures and the brackets from each other, wherein the bracket precursors and the support structures are monolithically formed, and wherein the method further comprises the step of providing a predetermined breaking point between the bracket precursors and the support structures.

2. The method of claim 1, wherein the bracket precursors are positioned in the machining device consecutively in a row.

3. The method of claim 2, wherein the archwire slot in each bracket precursor is provided by grinding, and wherein grinding is performed based on a linear relative movement between a grinding tool and the bracket precursors along the row.

4. The method of claim 2, wherein the archwire slot in each bracket precursor being provided by electrical discharge machining of multiple or all bracket precursors at a time using a generally linear structure or wire which extends along the row.

5. The method of claim 1, further comprising the steps of:
 building up the support structure using additive material manufacturing; and
 building up the bracket precursor on the support structure using additive material manufacturing.

6. The method of claim 5, wherein the step of building up the bracket precursors comprises building up a bracket bonding pad on the support structure and a bracket body precursor on the bonding pad.

7. The method of claim 6, wherein the bracket body precursor comprises an undersized slot forming a basis for providing the archwire slot by material removal from the bracket body precursor.

8. The method of claim 1, comprising the steps of:
 providing at least one virtual tooth surface of a patient;
 providing a virtual bracket comprising a virtual bracket bonding pad and a virtual bracket body, the virtual bracket bonding pad having a virtual tooth facing surface being associated to the virtual tooth surface;
 determining a geometric relationship between at least two of:
  an archwire position (or archwire slot position),
  the bracket position and
  a reference surface; and
 determining a geometry of a support structure based on the determined geometric relationship.

9. The method of claim 8, further comprising the step of creating the support structure between the reference surface and the virtual bracket bonding pad.

10. The method of claim 1, wherein the step of providing the bracket precursors involves three-dimensionally building up the bracket precursors in a three-dimensional build-up device which is based on Selective Laser Melting (SLM) or Stereo Lithography (STL).

11. The method of claim 8, wherein the step of providing the bracket precursors involves three-dimensionally building up the bracket precursors in a three-dimensional build-up device which is based on Selective Laser Melting (SLM) or Stereo Lithography (STL) and further comprising the steps of:
 providing a support plate which forms the reference surface;
 positioning the support plate in the build-up device; and
 building up the support structure and the bracket precursor.

12. The method of claim 11, further comprising the steps of:
 placing the support plate with the bracket precursors built up thereon in the machining device; and
 providing the bracket precursors with the archwire slot.

13. A customized orthodontic bracket, obtained from three-dimensionally building-up or casting and having an archwire slot obtained from material removal.

14. The method of claim 9, wherein the step of providing the bracket precursors involves three-dimensionally building up the bracket precursors in a three-dimensional build-up device which is based on Selective Laser Melting (SLM) or Stereo Lithography (STL) and further comprising the steps of:
 providing a support plate which forms the reference surface;
 positioning the support plate in the build-up device; and
 building up the support structure and the bracket precursor.

15. A method of making customized orthodontic brackets, the method comprising the steps of:
 providing a plurality of individually shaped customized orthodontic bracket precursors and one or more support structures, wherein a support structure is provided for each bracket precursor and wherein the support structure and bracket precursor are monotlithically formed;

positioning the bracket precursors with the support structure(s) in a machining device;

using the machining device to provide an archwire slot in each bracket precursor by material removal, thereby providing a plurality of archwire slots with the archwire slots aligned along a common path with each other, and thereby provide a plurality of brackets; and separating the support structure(s) and the brackets from each other, wherein the bracket precursors are positioned in the machining device consecutively in a row.

16. The method of claim 15, wherein the archwire slot in each bracket precursor is provided by grinding, and wherein grinding is performed based on a linear relative movement between a grinding tool and the bracket precursors along the row.

17. The method of claim 15, wherein the archwire slot in each bracket precursor is provided by electrical discharge machining of multiple or all bracket precursors at a time using a generally linear structure or wire which extends along the row.

* * * * *